United States Patent [19]

Anderson

[11] Patent Number: 5,083,868
[45] Date of Patent: Jan. 28, 1992

[54] COLORIMETER

[75] Inventor: Mark E. Anderson, Loveland, Colo.

[73] Assignee: Hach Company, Loveland, Colo.

[21] Appl. No.: 656,559

[22] Filed: Feb. 15, 1991

[51] Int. Cl.⁵ .................................................. G01J 3/51
[52] U.S. Cl. .................................... 356/402; D10/81;
356/414
[58] Field of Search ................................. 356/402–411,
356/244, 412–422, 432–435; D 24/216,
231–232; D 10/46, 81

[56] References Cited

U.S. PATENT DOCUMENTS

| | | | |
|---|---|---|---|
| 696,371 | 3/1902 | Grace | 356/419 |
| 1,495,763 | 5/1924 | Simpson et al. | 356/415 |
| 2,341,810 | 2/1944 | Peet | 356/415 |
| 4,304,490 | 12/1981 | Murakoshi et al. | 356/244 |
| 5,013,155 | 5/1991 | Rybak | 356/408 |

OTHER PUBLICATIONS

Beckman Instruments, "Beckman Beam Condenser for IR–4200", Scientific Instruments Division, 10/76.

Primary Examiner—F. L. Evans
Assistant Examiner—K. P. Hantis
Attorney, Agent, or Firm—Dean P. Edmundson

[57] ABSTRACT

An improved portable colorimeter is described in which there is a cap member detachably secured to a housing. The cap member can be placed in one position for enclosing the cell compartment for protection of the colorimeter during transport and storage. The cap can be placed in a second position over the cell compartment for preventing ambient light from entering the cell compartment during testing. In one embodiment the cap member rests in grooves adjacent the cell compartment during testing.

11 Claims, 6 Drawing Sheets

COLORIMETER

FIELD OF THE INVENTION

This invention relates to scientific instruments. More particularly, this invention relates to colorimetric instruments. Even more particularly, this invention relates to colorimeters which are portable and are intended for use in the field.

BACKGROUND OF THE INVENTION

It is common practice in the chemical field to analyze materials for contaminants and obtain the results using colorimetric instrumentation. Colorimetric instrumentation is an analytical method in which the color intensity of a substance, or a colored derivative thereof, is measured.

Such instrumentation is currently commonly used in laboratory facilities to provide scientists with specific information concerning concentration of various parameters. Although there are portable colorimeters available which can be used in the field for analysis, the size and bulk of such colorimeters are larger than desired for many applications.

There are commercial instruments for analysis on the market which use removable light shields to block ambient light which would disturb colorimetric measurements. However, these instruments do not functionally integrate the light shield into the device.

There are other instruments on the market which include a protective cover in the form of a hinged door. However, such doors are not also functional as light shields.

There has not heretofore been provided a portable colorimeter which includes a cover or cap which can be utilized both as a light shield and for protection of the instrument during transport and storage.

SUMMARY OF THE PRESENT INVENTION

In accordance with the present invention there is provided an improved portable colorimeter of the type including a housing, a cell compartment in the housing for receiving a sample to be tested, a light source, and a photodetector for detecting light transmitted through the sample from the light source. The improvement comprises a cap member which is carried by the housing. The cap is movable between first and second positions relative to the housing. When the cap is in the first position it encloses the cell compartment for protection of the colorimeter during transport and storage. When the cap is in the second position it prevents ambient light from entering the cell compartment and altering the test result when the sample is in the cell compartment for testing.

In the present invention the cap member functions in one position as protection for the delicate optics area of the colorimeter during transport and storage, and it functions in a second position as a light shield to prevent ambient light from interfering with test results. This combination of features is unique and has not heretofore been provided in prior devices.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
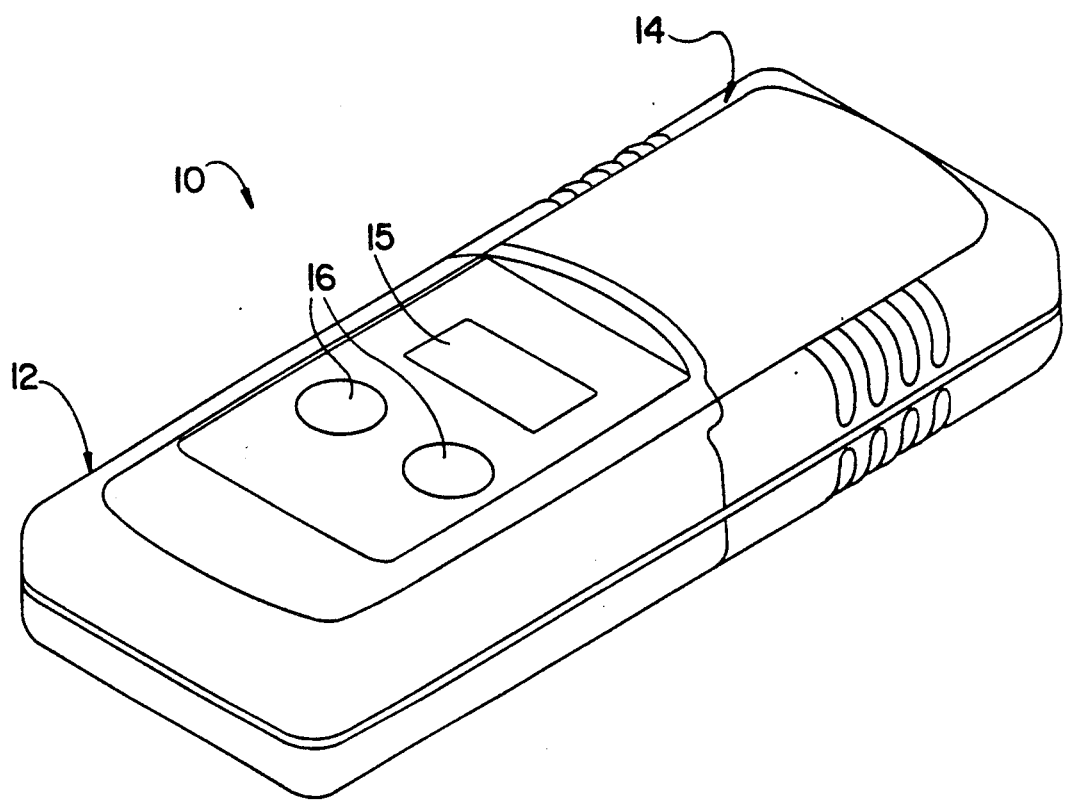
FIG. 1 is a perspective view of one embodiment of portable colorimeter of the invention.

In the drawings there is illustrated a preferred embodiment of portable colorimeter 10 of the invention which comprises a housing 12 and a detachable cap member or cover 14. Preferably the device includes the necessary light source (LED), battery, photodetector for measuring light transmitted through a sample being tested, a visual display 15 for read-out of appropriate test results, and buttons 16 for controlling operation of the colorimeter.

Figure 6:
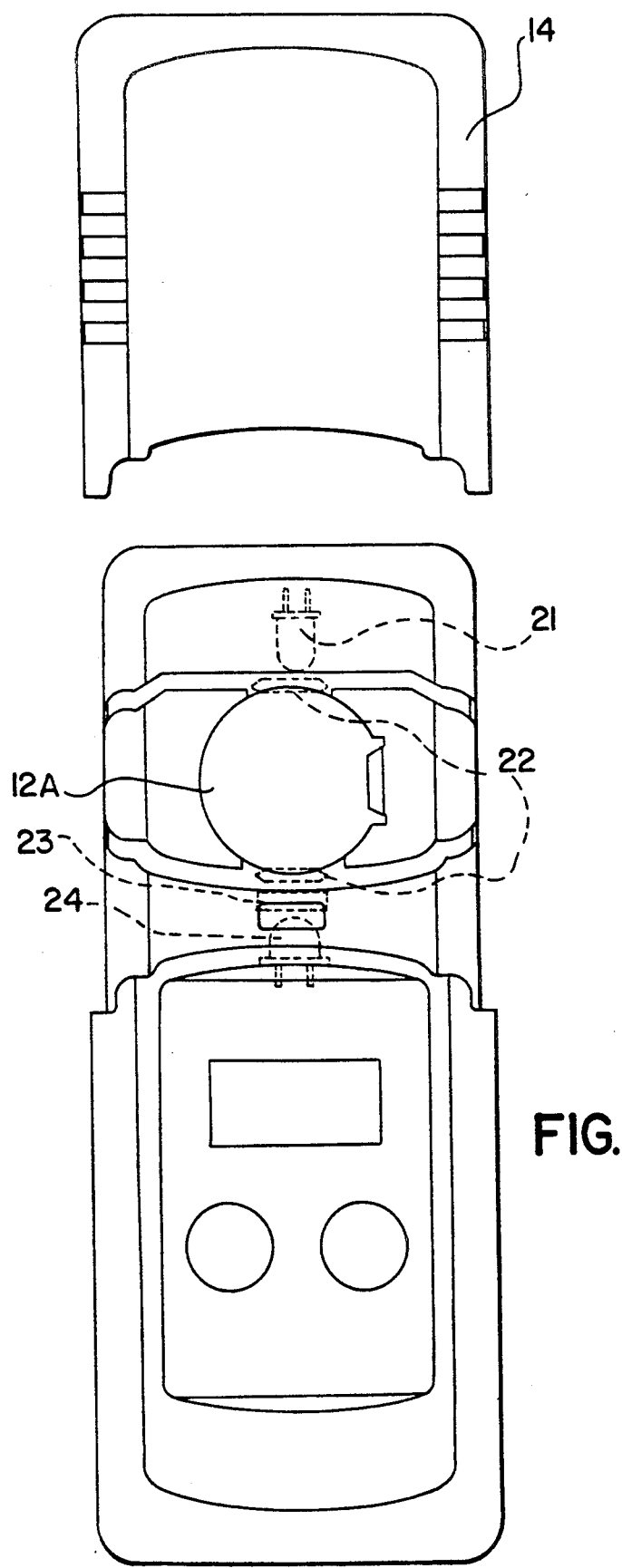
FIG. 6 is a top view of the colorimeter of FIG. 1 with the cap removed.

The housing includes a printed circuit board, a battery holder, and an optics assembly. The optics assembly (see FIG. 6) includes a light source 21, two transparent windows 22 for sample spill protection, an interference filter 23, and a photodetector 24. The sample compartment 12A is located between the light source and the photodetector, as illustrated.

Preferably the housing 12 is elongated (i.e., having a length greater than its width), and preferably the cap member 14 is also elongated and of the same width as the housing, as illustrated. Preferably the width and thickness of the colorimeter are such that the device can be easily carried in a pocket of the user.

Figure 2:
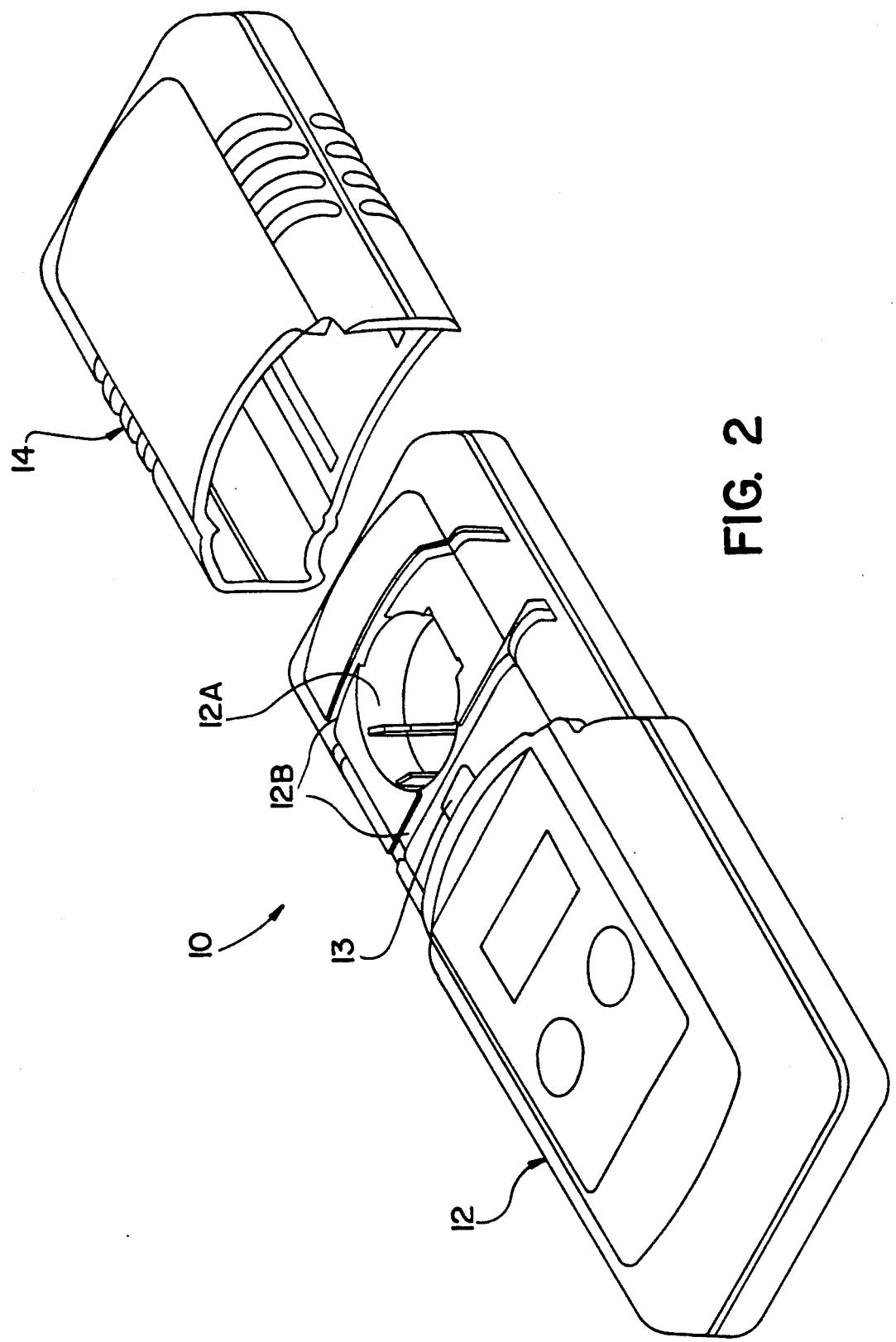
FIG. 2 is a perspective view of the embodiment of portable colorimeter of FIG. 1 with the cap member removed.
Figure 3:
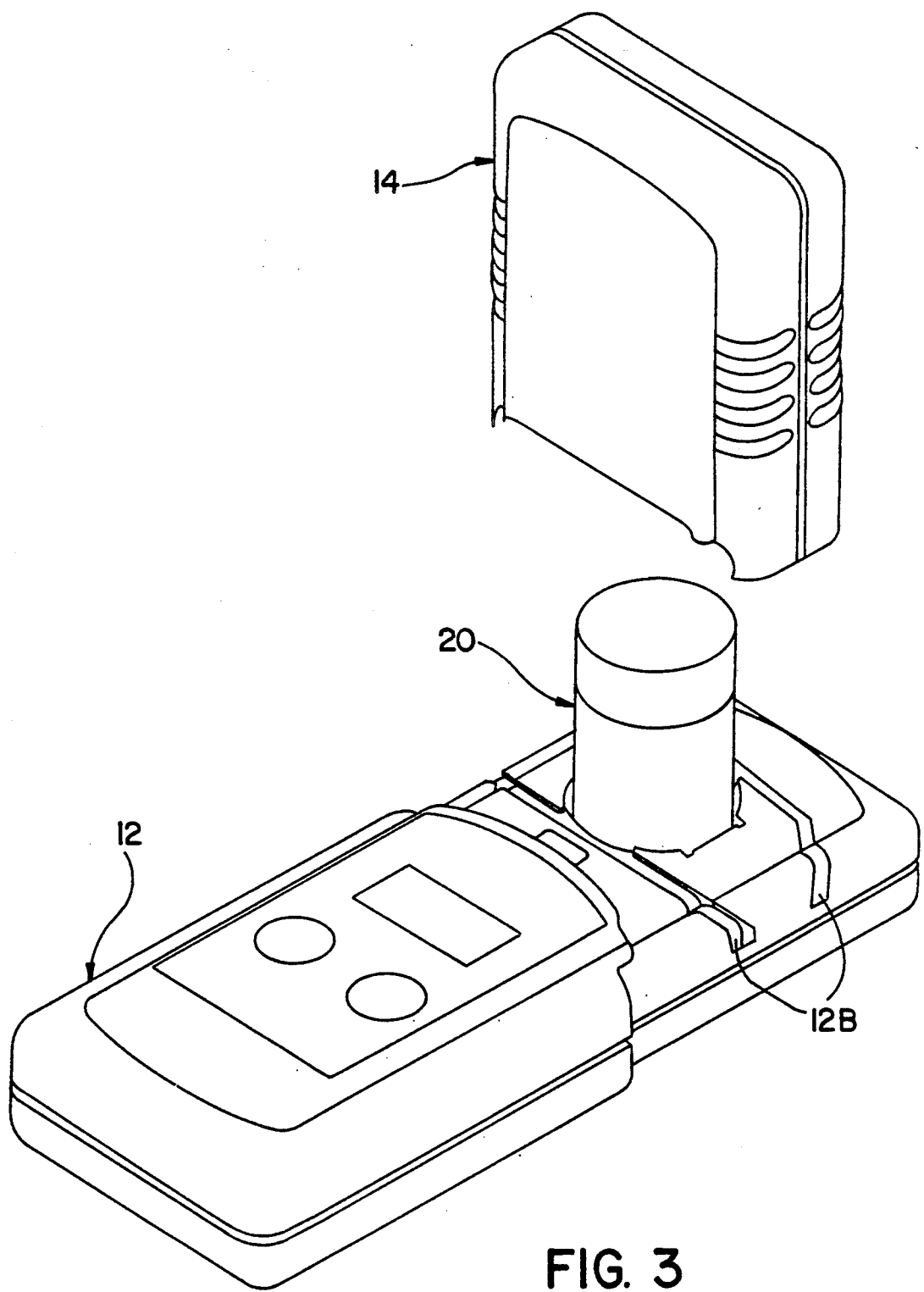
FIG. 3 is a perspective view of the portable colorimeter of FIG. 1 with a sample cell in the cell compartment.

The cap member 14 preferably slidably engages one end of the device. As shown in FIG. 2, the cap member slides off one end of the device along the longitudinal centerline of the housing. This then exposes the cell compartment 12A in which a sample cell or vial can be inserted for testing purposes (as illustrated in FIG. 3 where vial 20 containing a liquid sample to be tested has been inserted).

The cell compartment is optically located between the light source and the photodetector. See FIG. 6 and the description above.

Figure 4:
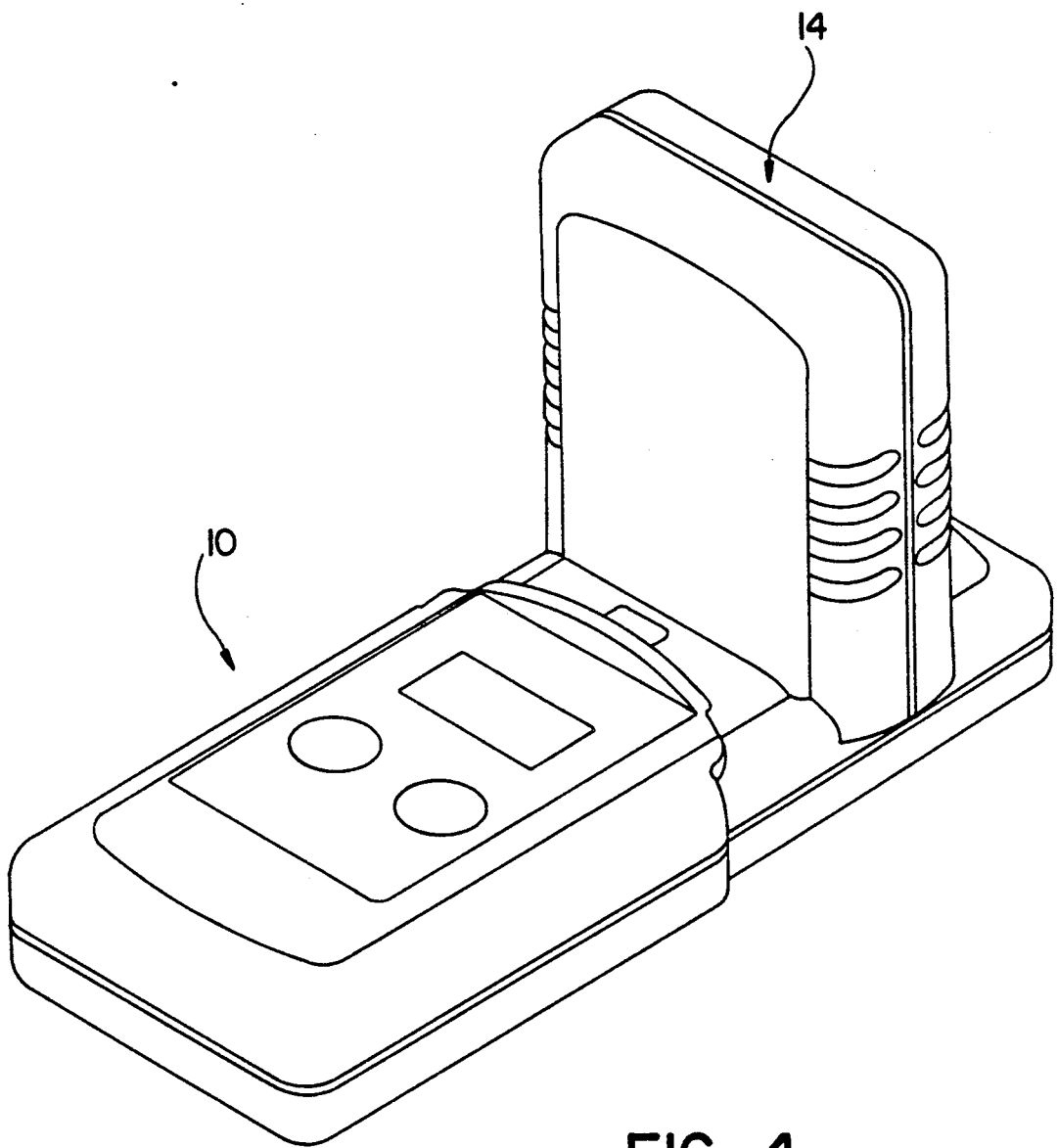
FIG. 4 is a perspective view of the portable colorimeter of FIG. 3 with the cap member covering the sample cell.
Figure 5:
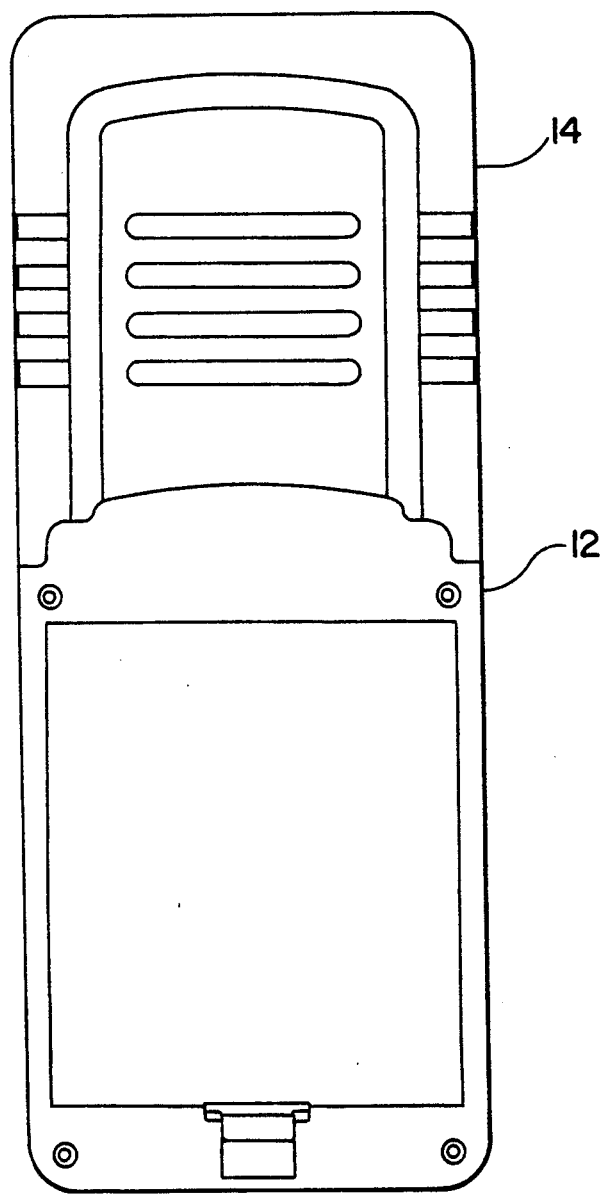
FIG. 5 is a bottom view of the portable colorimeter of FIG. 1.

Because ambient light can interfere with the test results obtained with a colorimeter, it is highly desirable to shield the cell compartment from ambient light during testing. In the colorimeter shown in the drawings this is accomplished simply and effectively with the cap member 14. Thus, as illustrated in FIG. 4, the cap member 14 is adapted to be positioned directly over the cell compartment. The cap surrounds and covers the upper portion of the vial 20 also. Preferably the longitudinal axis of the cap 14 is perpendicular to the longitudinal axis of the housing 12 when the cap is in the position shown in FIG. 4. The open end of the cap of course must be wider than the diameter of the sample vial so that the cap can fit over the upper portion of the vial.

To facilitate a good fit between the cap 14 and the housing 12 for light shielding purposes, it is preferable for the open end of the cap to be contoured complementarily to the upper surface of the housing, as illustrated in the drawings. It is also preferable for the upper surface of the housing to include spaced-apart grooves 12B, as illustrated, to receive the wall edges of the open end of the cap 14. The grooves are preferably located on opposite sides of the cell compartment as shown. The presence of the grooves for receiving the open end of the cap member also serves to stabilize the cap during testing.

The width and depth of the grooves may vary. The width of the grooves is only slightly larger than the thickness of the wall material of the cap member so that the wall of the cap fits snugly into the grooves. The depth of the grooves is preferably about 0.03 inch, but the depth may be greater if desired.

Preferably the cap member and the housing each include an appropriate detent to assist in holding the cap on the housing in the position shown in FIG. 1 for transport and storage. In FIG. 2 one such detent 13 is shown on the upper surface of the housing 12. Other means could also be used for this purpose.

To facilitate removal of the cap 14 from the housing 12 along the longitudinal axis of housing 12 (as shown in FIG. 2) it is preferable for the cap to include transverse indentations 14A on its outer surface, as illustrated in the drawings. The presence of these indentations renders the cap easier to grip with fingers when removing the cap.

The pocket colorimeter illustrated in the drawings is useful for testing for a wide range of parameters including, but not limited to, chlorine, bromine and nitrate, for example. A sample vial is first filled with a blank solution (usually an untreated sample). Another sample vial is filled with the sample solution to be tested. Then the appropriate reagent or chemical indicator is added to the vial containing the sample to be tested, followed by capping the vial and shaking the contents to assure good mixing. The vial containing the blank solution is placed into the cell compartment 12A, after which the vial is covered with cap 14 in the manner shown in FIG. 4. The instrument display is zeroed. Then the vial containing the sample to be tested is placed in the cell compartment in place of the vial containing the blank solution, followed by covering with the cap 14. Then another reading is obtained to indicate the light transmittance through the sample vial. Then the cap is lifted and the sample vial is removed. At the conclusion of testing the cap member can again be placed over the end of housing 12 to protect the cell compartment and the optics of the instrument during transport and storage.

Other variants are possible without departing from the scope of the present invention.

What is claimed is:

1. A portable colorimeter of the type including a housing, a cell compartment in said housing for receiving a sample to be tested, a light source, and a photodetector for detecting light transmitted through said sample from said light source, wherein the improvement comprises a cap member carried by said housing, said cap member being movable from a first position to a second position relative to said housing, wherein said cap member in said first position encloses said cell compartment for transport and storage of said colorimeter; and wherein said cap member in said second position prevents ambient light from entering said cell compartment when said sample is in said compartment for testing.

2. A portable colorimeter in accordance with claim 1, wherein said housing is elongated and includes first and second ends; and wherein said cap member slidably engages said first end of said housing.

3. A portable colorimeter in accordance with claim 2, wherein said cap member is detachable from said housing.

4. A portable colorimeter in accordance with claim 3, wherein said first end of said housing includes spaced-apart grooves on one surface thereof adjacent said cell compartment; wherein said cap member includes an open end and a closed end, and wherein said open end resides in said grooves when said cap member is in said second position.

5. A portable colorimeter in accordance with claim 4, wherein said cell compartment is located between said grooves.

6. A portable colorimeter in accordance with claim 5, wherein said colorimeter further includes a light-transparent vial for containing said sample to be tested.

7. A portable colorimeter in accordance with claim 1, wherein said colorimeter further includes a visual display for displaying test results.

8. A portable colorimeter of the type including a housing, a sample cell, a cell compartment in said housing for receiving said sample cell, a light source, a battery, and a photodetector for detecting light transmitted through said sample from said light source, wherein the improvement comprises a cap member detachably secured to said housing, said cap member being movable from a first position to a second position relative to said housing, wherein said cap member in said first position encloses said cell compartment for transport and storage of said colorimeter; and wherein said cap member in said second position prevents ambient light from entering said cell compartment when said sample is in said compartment for testing.

9. A portable colorimeter in accordance with claim 8, wherein said housing is elongated and includes first and second ends; and wherein said cap member slidably engages said first end of said housing.

10. A portable colorimeter in accordance with claim 9, wherein said first end of said housing includes spaced-apart grooves on one surface thereof adjacent said cell compartment; wherein said cap member includes an open end and a closed end, and wherein said open end resides in said grooves when said cap member is in said second position.

11. A portable colorimeter in accordance with claim 10, wherein said cell compartment is located between said grooves.

* * * * *